US009414765B2

(12) United States Patent
Miyazaki et al.

(10) Patent No.: US 9,414,765 B2
(45) Date of Patent: Aug. 16, 2016

(54) FRESH BLOOD IMAGING (FBI) WITH INDEPENDENTLY CONTROLLED MRI DATA ACQUISITION PARAMETERS FOR DIASTOLIC AND SYSTOLIC MRI ACQUISITION SUB-SEQUENCES

(75) Inventors: Mitsue Miyazaki, Mount Prospect, IL (US); Andrew J. Wheaton, Shaker Heights, OH (US)

(73) Assignee: Toshiba Medical Systems Corporation, Tochigi-Ken (JP)

( * ) Notice: Subject to any disclaimer, the term of this patent is extended or adjusted under 35 U.S.C. 154(b) by 773 days.

(21) Appl. No.: 13/415,188

(22) Filed: Mar. 8, 2012

(65) Prior Publication Data
US 2013/0234707 A1    Sep. 12, 2013

(51) Int. Cl.
| G01R 33/48 | (2006.01) |
| G01R 33/44 | (2006.01) |
| A61B 5/055 | (2006.01) |
| A61B 5/026 | (2006.01) |
| G01R 33/563 | (2006.01) |
| A61B 5/0456 | (2006.01) |
| G01R 33/561 | (2006.01) |
| G01R 33/567 | (2006.01) |

(52) U.S. Cl.
CPC ............. A61B 5/055 (2013.01); A61B 5/0263 (2013.01); G01R 33/5635 (2013.01); *A61B 5/0456* (2013.01); *G01R 33/5617* (2013.01); *G01R 33/5673* (2013.01)

(58) Field of Classification Search
CPC .......... G01R 33/5635; G01R 33/5617; G01R 33/5673; A61B 5/0263; A61B 5/0456; A61B 5/055

USPC ........................... 324/300–322; 600/407–420
See application file for complete search history.

(56) References Cited

U.S. PATENT DOCUMENTS

| 4,891,594 | A  | * | 1/1990 | Wilfley et al. ................ 324/309 |
| 6,801,800 | B2 |   | 10/2004 | Miyazaki et al. |
| 2008/0161678 | A1 | * | 7/2008 | Miyazaki et al. ............. 600/419 |
| 2008/0265884 | A1 | * | 10/2008 | Miyazaki ....................... 324/309 |
| 2011/0115484 | A1 | * | 5/2011 | Lee et al. ....................... 324/309 |

(Continued)

FOREIGN PATENT DOCUMENTS

| JP | 2001-061812 A | 3/2001 |
| JP | 2007-111513 A | 5/2007 |

(Continued)

OTHER PUBLICATIONS

Miyazaki, Mitsue, and Vivian S. Lee. "Nonenhanced MR Angiography 1." Radiology 248.1 (2008): 20-43.*

(Continued)

*Primary Examiner* — Melissa Koval
*Assistant Examiner* — Rishi Patel
(74) *Attorney, Agent, or Firm* — Nixon & Vanderhye, P.C.

(57) ABSTRACT

A magnetic resonance imaging (MRI) is configured to effect magnetic resonance angiography (MRA) data acquisition sequences including electrocardiogram (ECG) triggered fresh blood imaging (FBI) images respectively associated with systolic and diastolic phases of ECG cycles. An operator input and display interface may be configured to provide operator options for independently controlling at least one imaging sequence parameter to have a different value for each of systolic and diastolic phase images in an FBI MRI data acquisition sequence.

22 Claims, 9 Drawing Sheets

(56) References Cited

U.S. PATENT DOCUMENTS

2011/0148413 A1* 6/2011 Miyazaki et al. ............. 324/309
2012/0212222 A1* 8/2012 Subramanian et al. ....... 324/309

FOREIGN PATENT DOCUMENTS

JP          2011-143241 A      7/2011
WO       2011/090089 A1    7/2011

OTHER PUBLICATIONS

Miyazaki, et al., "Non-Contrast-Enhanced MR Angiography Using 3D ECG-Synchronized Half-Fourier Fast Spin Echo," *Journal of Magnetic Resonance Imaging*, 12:776-783 (2000).

Miyazaki, et al., "Peripheral MR Angiography: Separation of Arteries from Veins with Flow-spoiled Gradient Pulses in Electrocardiography-triggered Three-dimensional Half-Fourier Fast Spin-Echo Imaging," *Radiology*, 227:890-896 (Jun. 2003).

Lim, et al., "3D Nongadolinium-Enhanced ECG-Gated MRA of the Distal Lower Extremities: Preliminary Clinical Experience," *Journal of Magnetic Resonance Imaging*, 28:181-189 (2008).

Lim, et al., "Three-dimensional Electrocardiographically Gated Variable Flip Angle FSE Imaging for MR Angiography of the Hands at 3.0 T: Initial Experience," *Radiology*, 252:874-881 (2009).

Storey, et al., "Tailoring the Flow Sensitivity of Fast Spin-Echo Sequences for Noncontrast Peripheral MR Angiography," *Magnetic Resonance in Medicine*, 64:1098-1108 (2010).

Nakamura, et al., "Noncontrast-enhanced Peripheral MRA: Technical Optimization of Flow-Spoiled Fresh Blood Imaging for Screening Peripheral Arterial Diseases," *Magnetic Resonance in Medicine*, 65:595-602 (2011).

Li, et al., "Unenhanced calf MR angiography at 3.0 T using electrocardiography-gated partial-fourier fast spin echo imaging with variable flip angle," *Eur. Radiol.*, 21:1311-1322 (2011).

International Search Report dated Apr. 16, 2013, re PCT/JP 2013/056367.

* cited by examiner

BA(DIASTOLE) - DA(SYSTOLE) = FS-FBI IMAGE

700 — ☐ MRI SEQUENCE TYPE = (DEFAULT=FSE)

| RO GRADIENT SPOILER MAGNITUDE | RF REFOCUSING ANGLE |
|---|---|
| SYSTOLIC SUB-SEQUENCE = X% (FLOW DE-PHASING) | SYSTOLIC SUB-SEQUENCE = A° |
| DIASTOLIC SUB-SEQUENCE = Y% (FLOW COMPENSATION) | DIASTOLIC SUB-SEQUENCE = B° |

$X = $ ______ 702
$Y = $ ______ 704
$A = $ ______ 706
$B = $ ______ 708

| AREA OF INTEREST | RO%Δ | AREA OF INTEREST |
|---|---|---|
| 710 ☐ ILIAC | X=+10%; Y=0% | A=140°; B=170° |
| 712 ☐ FEMORAL (THIGH) | X=+20%; Y=0% | A=130°; B=170° |
| 714 ☐ CALF | X=+25%; Y=0% | A=120°; B=170° |

716 — ☐ CHANGE X,Y,A,B?
718 — ☐ ADDITIONAL PE GRADIENT SPOILER?
    PE = __% FOR SYSTOLIC, __% FOR DIASTOLIC
720 — ☐ STORE REVISED X,Y,A,B VALUES?
    • STORE AS: (DEFAULT OR SPECIFIED FILE NAME)

GUI DISPLAY SCREEN
FOR FS-FBI

FRESH BLOOD IMAGING (FBI) WITH INDEPENDENTLY CONTROLLED MRI DATA ACQUISITION PARAMETERS FOR DIASTOLIC AND SYSTOLIC MRI ACQUISITION SUB-SEQUENCES

FIELD

The subject matter below relates generally to magnetic resonance imaging (MRI) apparatus and method for Fresh Blood Imaging (FBI).

DETAILED DESCRIPTION

In an exemplary embodiment, MRI data acquisition parameters for diastolic and systolic MRI acquisition sub-sequences are independently controlled to produce different flip angles of RF refocusing pulses when capturing cardiac-triggered systolic and diastolic images in an overall Flow-Spoiled Fresh Blood Imaging (FS-FBI) data acquisition sequence using a fast-spin-echo (FSE) MRI acquisition method to provide improved magnetic resonance angiography (MRA). For example, the MRI system controller in this exemplary embodiment incorporates a graphical user interface (GUI) which facilitates optimization of read-out (RO) magnetic gradient flow-spoiler pulse magnitudes and refocusing RF (radio frequency) pulse amplitudes while using FSE MRI in an FS-FBI MRA context. Of course, the system controller could also be configured to automatically use different such systolic and diastolic sub-sequence parameters during FS-FBI (e.g., even without such a flexible GUI).

Figure 1:
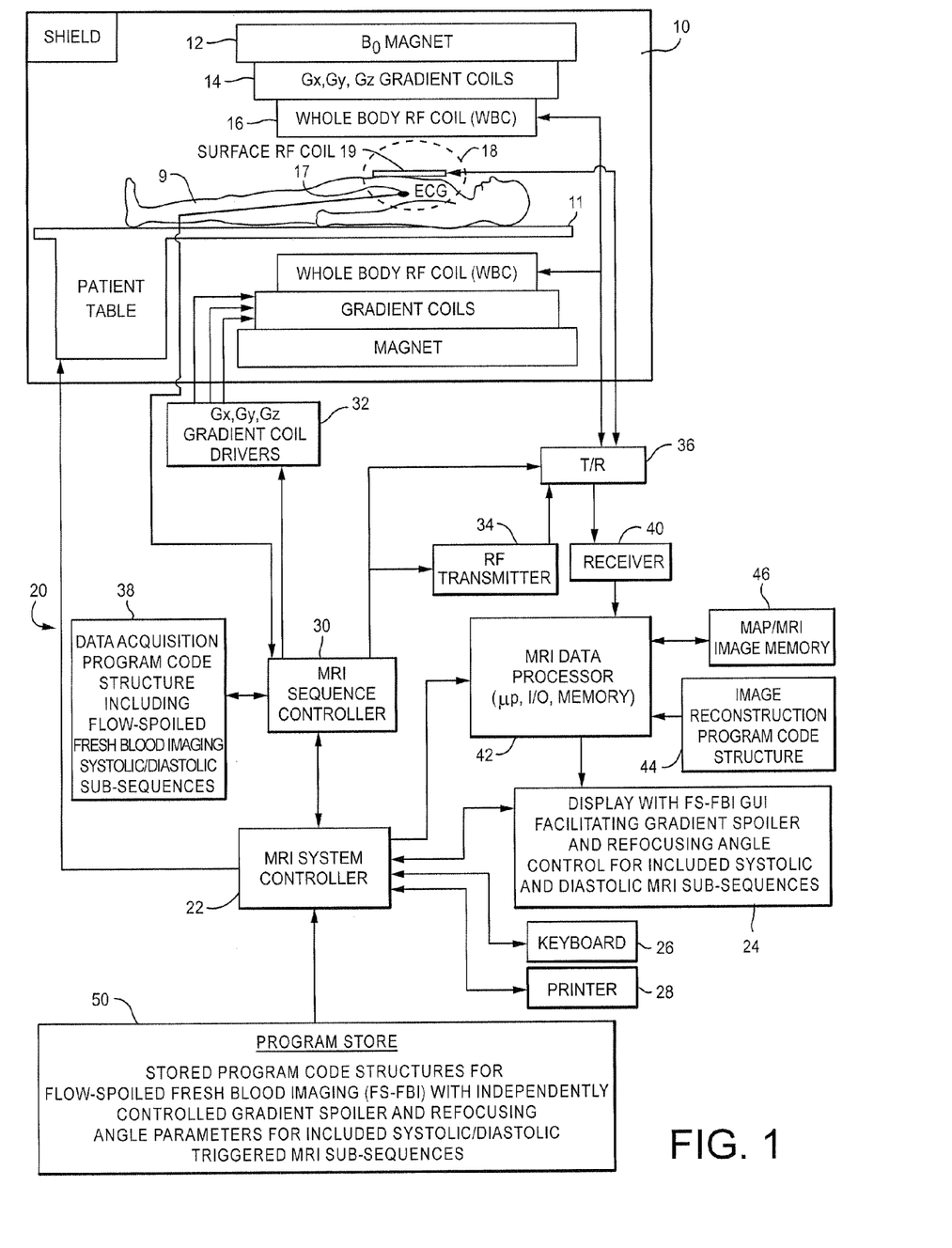
FIG. 1 is a high-level schematic block diagram of an exemplary MRI system configured to acquire and process MRI image data using an FS-FBI (Flow Spoiled Fresh Blood Imaging) operator interface that permits independent control of plural MRA parameters (e.g., gradient flow-spoiler and RF refocusing angle parameters when using fast-spin-echo (FSE) MRI acquisition sequences) for both systolic and diastolic MRI sub-sequences in FBI.

The exemplary MRI system shown in FIG. 1 includes a gantry 10 (shown in schematic cross-section) and various related system components 20 interfaced therewith. At least the gantry 10 is typically located in a shielded room. The exemplary MRI system geometry depicted in FIG. 1 includes a substantially coaxial cylindrical arrangement of the static field $B_0$ magnet 12, a $G_x$, $G_y$ and $G_z$ gradient coil set 14 and a large whole body RF coil (WBC) assembly 16. Along the horizontal axis of this cylindrical array of elements is an imaging volume 18 shown as substantially encompassing the thoracic area of a patient 9 supported by a patient table 11. A smaller surface RF coil 19 (which may be an array that extends (wholly or partially) around the patient) is more closely coupled to the patient region of interest (ROI) in image volume 18. As those in the art will appreciate, compared to the whole body coil (WBC), relatively small coils and/or arrays such as surface coils or the like are often customized for particular body parts (e.g., arms, shoulders, elbows, wrists, knees, legs, chest, spine, etc.).

One or more electrocardiogram (ECG) electrodes 17 (or other trigger signal capturing connections, e.g., for peripheral triggering as known in the art) may be coupled to the patient to provide an ECG input to the system 20. This permits, for example, cardiac-triggered MRI sequences synchronized with desired portions of the cardiac cycle as will be appreciated by those in the art.

An MRI system controller 22 has input/output ports connected to display 24, keyboard 26 and printer 28. As will be appreciated, the display 24 may be of the touch-screen variety so that it provides control inputs as well. In this exemplary embodiment, the display provides an FS-FBI GUI that facilitates separate independent control of magnetic gradient flow-spoiler and refocusing angle parameters for each of the systolic and diastolic cardiac-triggered MRI sub-sequences used in FS-FBI.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing preparatory and diagnostic MRI data acquisition sequences (e.g., including FS-FBI sequences in conjunction with other (e.g., conventional diagnostic) MRI sequences already available in the repertoire of the MRI sequence controller 30).

The MRI system 20 includes an RF receiver 40 providing input to data processor 42 so as to create processed image data, which is sent to display 24. The MRI data processor 42 is also configured for access to image reconstruction program code structure 44 and to MAP and MRI image memory 46 (e.g., for storing image data derived from processing in accordance with the image reconstruction program code structure 44).

Also illustrated in FIG. 1 is a generalized depiction of an MRI system program store 50 where stored program code structures (e.g., for FS-FBI with independently controlled gradient flow-spoiler and refocusing angle parameters for each of the included systolic and diastolic MRI sub-sequences) are stored in non-transitory computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments described hereinbelow. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic or solid state semiconductor storage media) is transformed from one state to another during operation of such a system. For example, at the conclusion of an imaging reconstruction process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient anatomy over an imaged volume space). As those in the art will appreciate, such arrays of stored data values represent and also constitute a physical structure—as does a particular structure of computer control program code that includes executable instructions which, when sequentially loaded into instruction registers and executed by one or more CPUs of the MRI system 20, cause a particular sequence of operational states to occur and be transitioned through within the MRI system.

The exemplary embodiments described below provide improved ways to process MRI data acquisitions and/or to generate and display MR images.

Non-contrast-enhanced MRA (NC-MRA) using cardiac-triggered 3D FSE-based techniques (FBI, NATIVE-SPACE, TRANCE) has been used for peripheral MRA applications. This class of NC-MRA methods leverages the inherent sensitivity of FSE to flow-induced spin dephasing. In general, a dark artery (DA) scan is acquired during systole while blood velocity is highest and a bright artery (BA) scan is acquired during diastole with relatively slow arterial flow. The angiogram is generated by subtracting the DA image data from the BA image data (on a pixel-by-pixel basis), thus cancelling static background signal.

Figure 9:
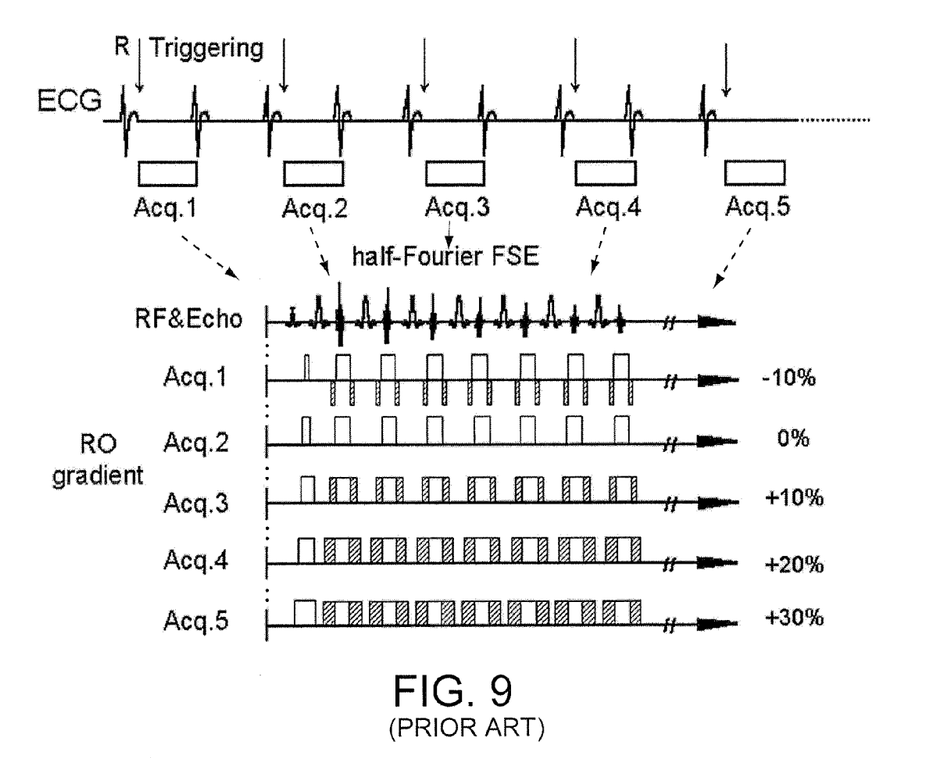
FIGS. 9-10 schematically depict prior art FS-FBI data acquisition sequences using read-out (RO) magnetic gradient flow-spoiling pulses of different magnitudes for successive FS-FBI acquisition sequences—but having the same magnitude for the systolic and diastolic sub-sequences within a given FS-FBI acquisition sequence.

FIG. 9 provides a prior art MRI sequence diagram depicting flow preparation imaging acquisitions, wherein the RO magnetic gradient associated with successive spin echoes in a FSE MRI data acquisition sequence is changed for successive acquisition cycles so as to acquire images with different flow-spoiling effects. The RO spoiler effective pulse magnitudes are described as a percentage for incrementing the effective value of the RO gradient pulse, where the area of the regular FSE non-spoiling RO gradient to the echo center represents a 100% "normal" gradient pulse magnitude. As those in the art will understand, the effective "magnitude" of the gradient pulse is actually represented by the area of the pulse envelope.

However in such prior art approaches, the RO gradient magnitude for any given acquisition cycle remained constant for the systolic and diastolic sub-sequences therewithin.

Figure 10:
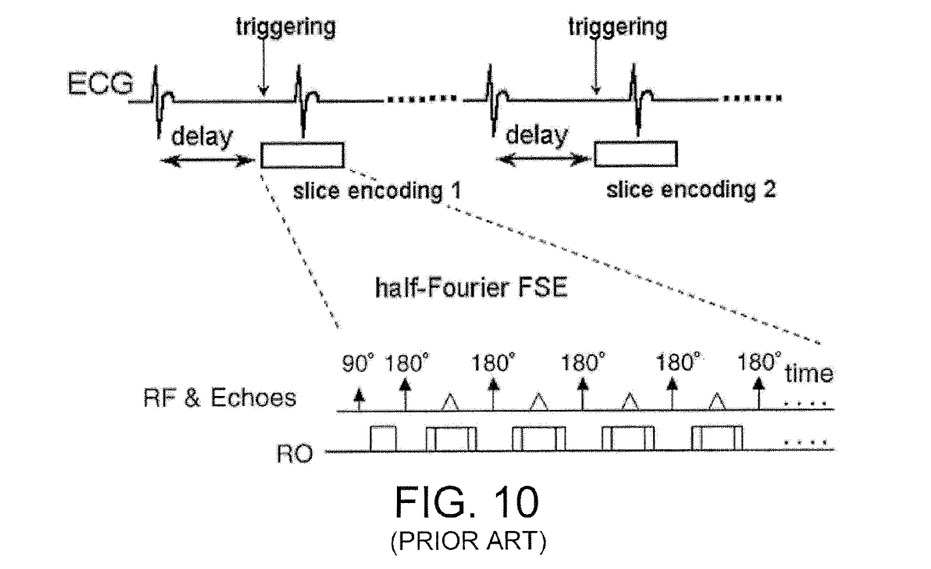

FIG. 10 provides a more detailed depiction of one of the prior art acquisition sequences shown in FIG. 9 for an FS-FBI MRI data acquisition sequence showing a more detailed depiction of the initial RF 90° spin nutation (i.e., "excitation") pulse, subsequent RF 180° spin refocusing pulses and interspersed RF spin-echo signals elicited from the patient. The RO magnetic gradient pulses associated with each elicited spin echo (including an added flow-spoiling component shown on either side of all but the first RO gradient pulse in the sequence) are also depicted.

That is, as those in the art will appreciate, cardiac-triggering is used in finer detail to acquire data during systole for a DA image and during diastole for a BA image in FS-FBI—during which, for any given overall acquisition sequence a constant RO gradient flow-spoiler pulse magnitude was used.

As those in the art will also appreciate, FS-FBI typically uses differently valued dephase/rephase gradient pulses for each of systolic and diastolic phase images (i.e., the strength of the dephase pulses is different from that of the rephase pulses). The intensities of the dephase pulses and rephase pulses are typically controlled according to fluid flow speeds being imaged (e.g., see U.S. Pat. No. 6,801,800 at 28:24-38 and FIGS. 23A-B).

The optimum RO spoiler gradient pulse effective magnitude can be optimized for many different conditions. For example, the effective magnitude may be optimized in one way for healthy (young) persons and in another way for more elderly patients—and/or for various ROIs as shown for one possible example in the table just below (noting that these preliminary example values for a given ETS and/or other parameter values may change for a different ETS value and/or different other parameter values):

| | Systolic Read-Out (RO) spoiler strength (%) | |
|---|---|---|
| Region of Interest (ROI) | Healthy (Young) Person | Elderly Patient |
| Aortoiliac | −10 | 0 |
| Femoral | 0 | +10 |
| Popliteocrural | +10 | +20 |

In addition to the RO gradient flow-spoiler, one may also wish to have some amount of PE magnetic gradient flow-spoiler. Depending upon the vessel orientation with respect to RO/PE directions, some vessels may be running obliquely to the RO direction and, in that case, a small amount of PE spoiler may help depict the vessel.

Figure 7A:
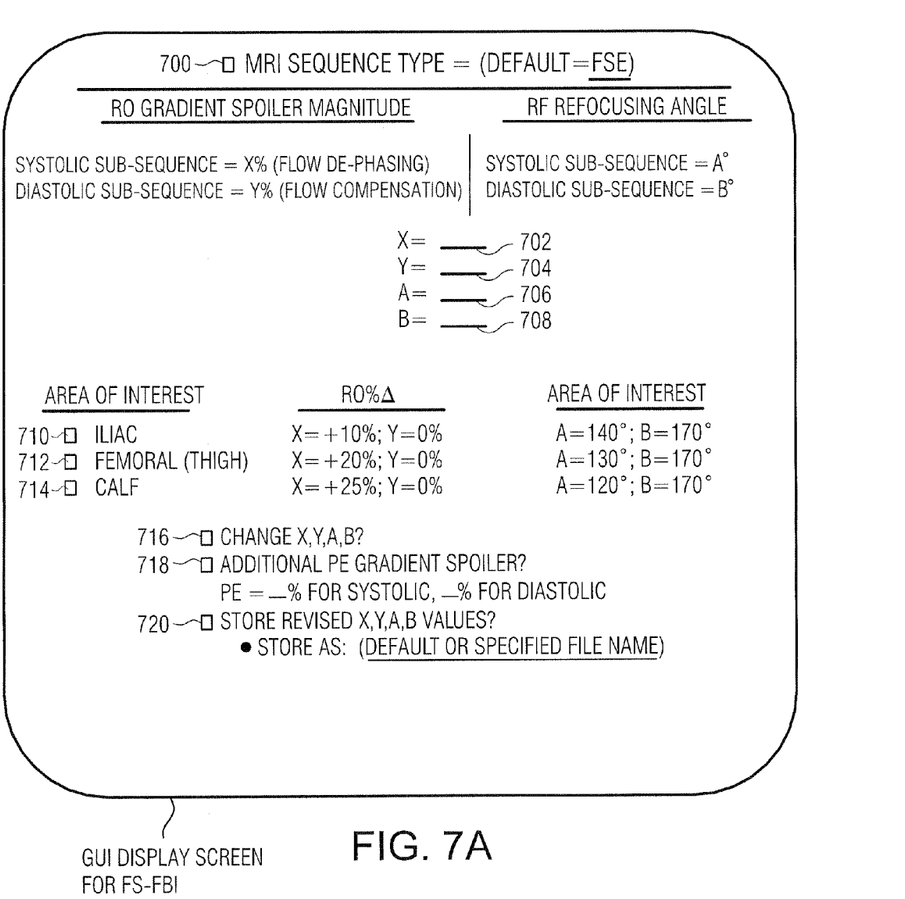
FIG. 7A schematically depicts an exemplary graphical user interface (GUI) which facilitates independent gradient flow-spoiler and refocusing angle control for each of the systolic and diastolic MRI sub-sequences used in fresh blood imaging (FBI) MRA.

The examples of some possible default parameter values for systolic and diastolic MRI subsequences in FSE FS-FBI depicted in the exemplary GUI embodiment of FIG. 7A were values used for some healthy volunteers with an MRI system having a main static magnet strength of 1.5 Tesla. For patients with diseases, the default values may, for example, have an added 10% to the RO gradient flow-spoiler pulse magnitudes shown in FIG. 7A.

Figure 2:
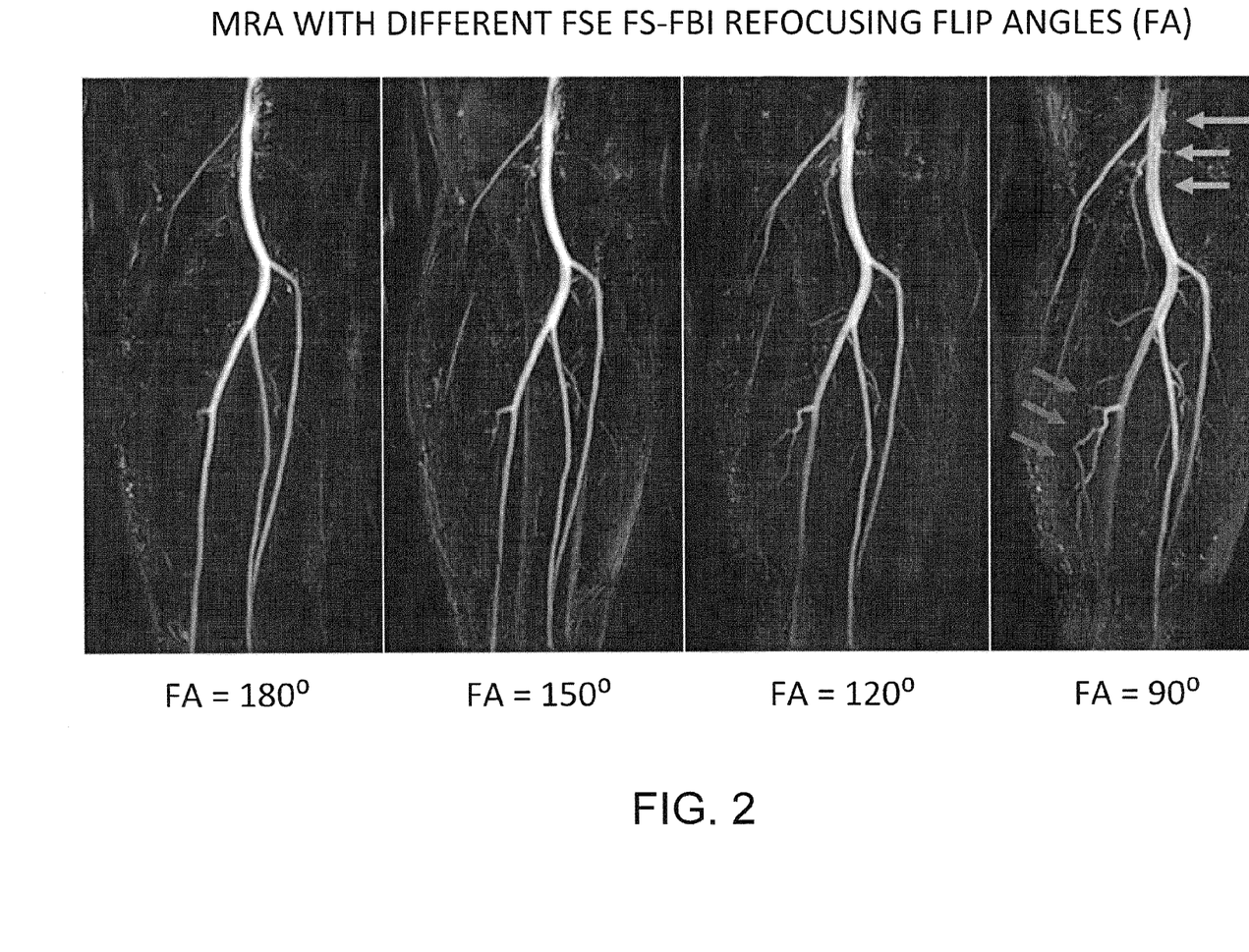
FIG. 2 is a composite of MRA images using different refocusing angles to demonstrate how flowing NMR magnetization spin signal is sensitive to refocusing angle.

Others have also already noted that the sensitivity of FSE to flow can also be tuned by adjusting the refocusing angle. In general, the lower the refocusing angle, the more sensitive FSE is to flow velocity. As demonstrated in FIG. 2, flowing spin signal is sensitive to refocusing angle. High refocusing angle maintains signal from flowing spins (in FBI subtraction image: large (fast) vessels good, small (slow) vessels bad), while low refocusing angle loses signal (in FBI subtraction image: small (flow) vessels good, large (fast) vessels bad).

Figure 3:
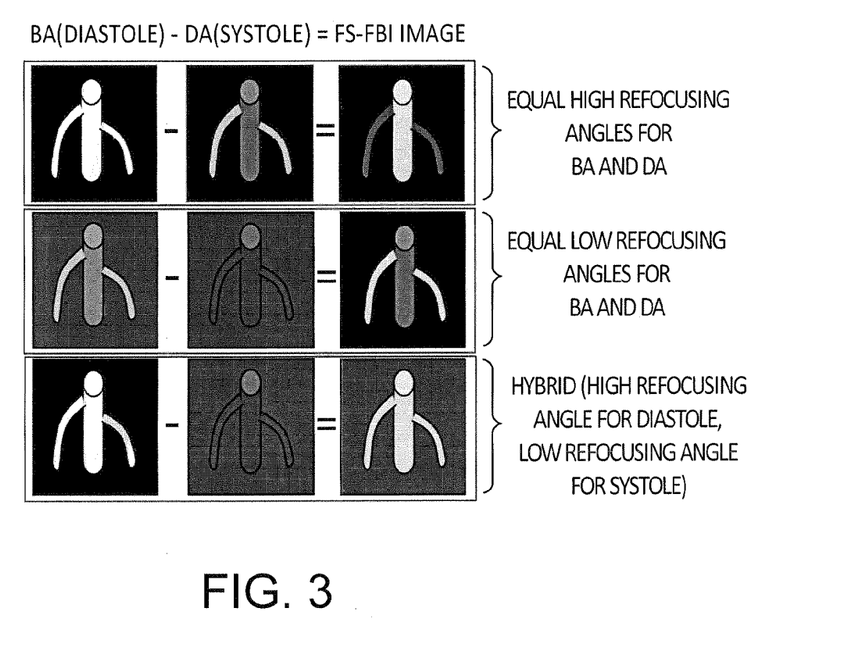
FIG. 3 schematically illustrates the effect of refocusing angles on gated 3D FSE (three-dimensional fast-spin-echo) MRA images.

FIG. 3 illustrates the effect of refocusing angle on gated 3D FSE. Left column: BA (diastole) data. Middle column: DA (systole) data. Right column: subtraction angiogram. Top row: high refocusing angle. Middle row: low refocusing angle. Bottom row: hybrid angle method (high refocusing angle in diastole, low refocusing angle in systole). The differences in background grayscale represent the effect of refocusing angle on background tissue and its subsequent subtraction.

Using a high refocusing angle (160°+) produces bright arteries in BA data, but also refocuses more arterial signal in the DA data, especially in slower flow branch arteries. Thus, the subtraction angiogram contains bright signal for larger, faster flow arteries, but weak signal for smaller, slower flow arteries (FIG. 3: top row). If a low refocusing angle (<120°) is used, large artery signal is reduced in BA data, but smaller, slower flow arteries are less affected. In the DA scan, even the small arteries are dark due to the combination of faster flow and low refocusing angle. Thus, a low refocusing angle produces an angiogram with bright signal in small branch arteries, but weak signal in larger arteries (FIG. 3: middle row).

All tissue signals are affected by the choice of refocusing angle, but due to the motion sensitivity of FSE, arterial signal is more sensitive to refocusing angle than venous or background signals. It is, therefore, now proposed to use different refocusing angles in the DA vs. BA acquisitions to produce more uniform contrast across all arterial branches without introducing deleterious amounts of background signal (FIG. 3: bottom row).

To illustrate this technique, data were acquired on the peripheral anatomy of a male volunteer using a 3T whole-body research system under IRB approval. Coronal partial-Fourier 3D FSE was acquired with peripheral pulse triggering using the following parameters: TE=60 ms, TR=3 RR, echo space=5.0 ms, readout BW=651 Hz/pixel, 2 shots, ETL=76, matrix=256×256, field-of-view (FOV)=35×35 cm, and forty 3.0 mm partitions. The DA and BA data were acquired as one continuous acquisition without interruption. The 3D FSE data were repeated seven times for the following BA:DA refocusing angle combinations: 160°:160°, 140°:140°, 120°:120°, 100°:100°, 160°:140°, 160°:120°, 160°:100°.

Figure 4:
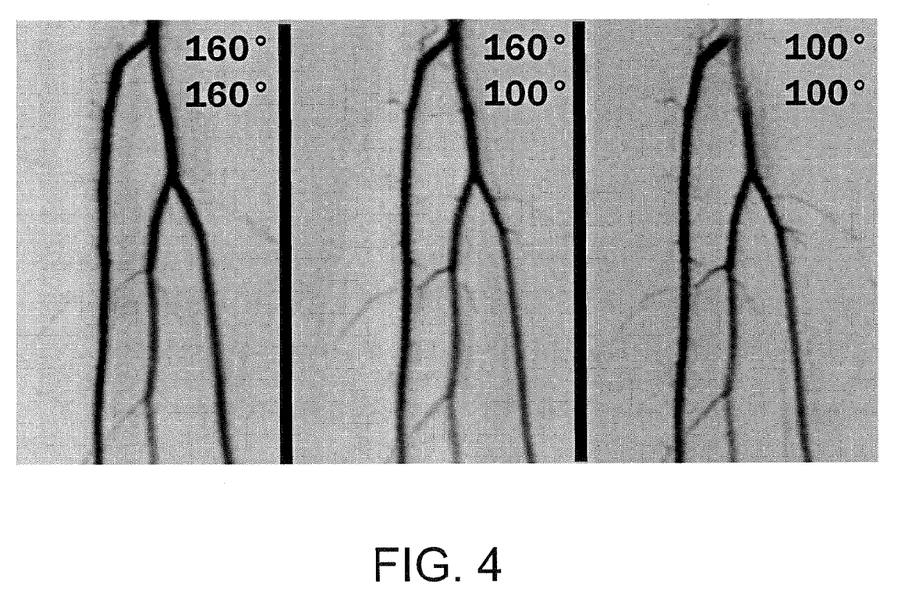
FIG. 4 is a composite of images illustrating added fine gauge detail provided by low refocusing angle data.
Figure 5:
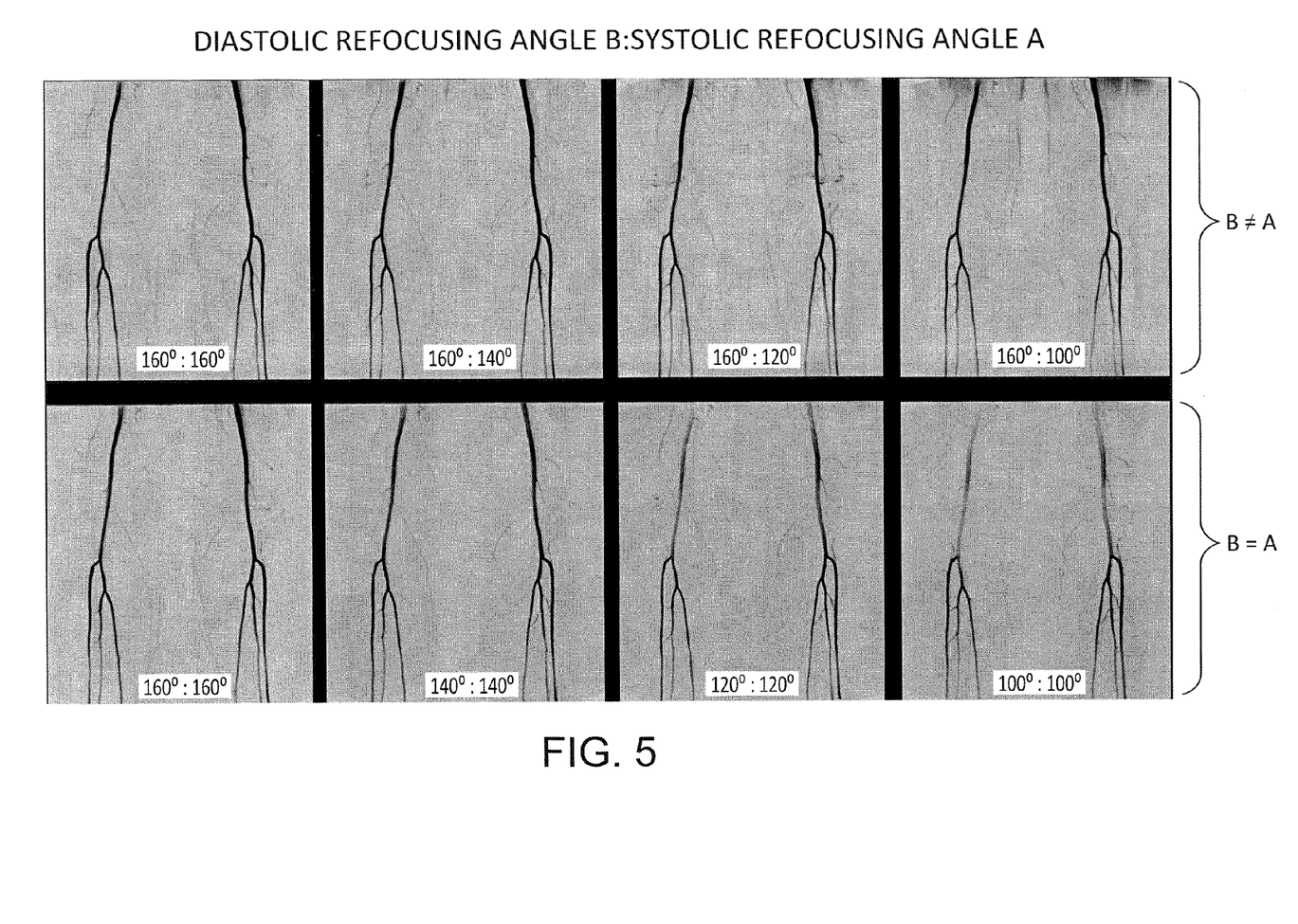
FIGS. 5 and 6 provide composite images comparing constant systolic refocusing angles versus hybrid refocusing angles where refocusing angles change for systolic sequences as well as diastolic sequences in FBI.

The hybrid angle angiograms maintained vessel contrast in large arteries across the range of DA refocusing angles (100° to 160°) (FIG. 5: top row). The larger the disparity between BA and DA, the greater the intrusion of background signal, especially near the edges of the FOV. The constant refocusing angle data (FIG. 5: bottom row) demonstrated a monotonic reduction of femoral artery signal with decreasing refocusing angle. The background signal remained consistently near zero in the constant refocusing angle sets. The fine gauge arteries, especially branches of the peroneal and anterior tibial arteries, are more visible on the lower refocusing angle data sets (FIG. 4). The low DA refocusing angle hybrid data sets (160°:120° and 160°:100° in FIG. 5) depicted comparable small artery detail as the constant low refocusing angle data sets (FIG. 4).

The hybrid angle method produced angiograms that maintained signal in large arteries while providing the fine arterial detail of low refocusing angle gated 3D FSE. This increase in uniformity came at the modest cost of slightly increased background signal. The hybrid angle method has the added advantage of reducing SAR relative to a constant high refocusing angle.

This preliminary study focused on evaluating the feasibility of using hybrid refocusing angles for gated 3D FSE. Based on this preliminary data, the 160°:120° pair offers fine arterial detail with less potential for background intrusion.

Figure 6:
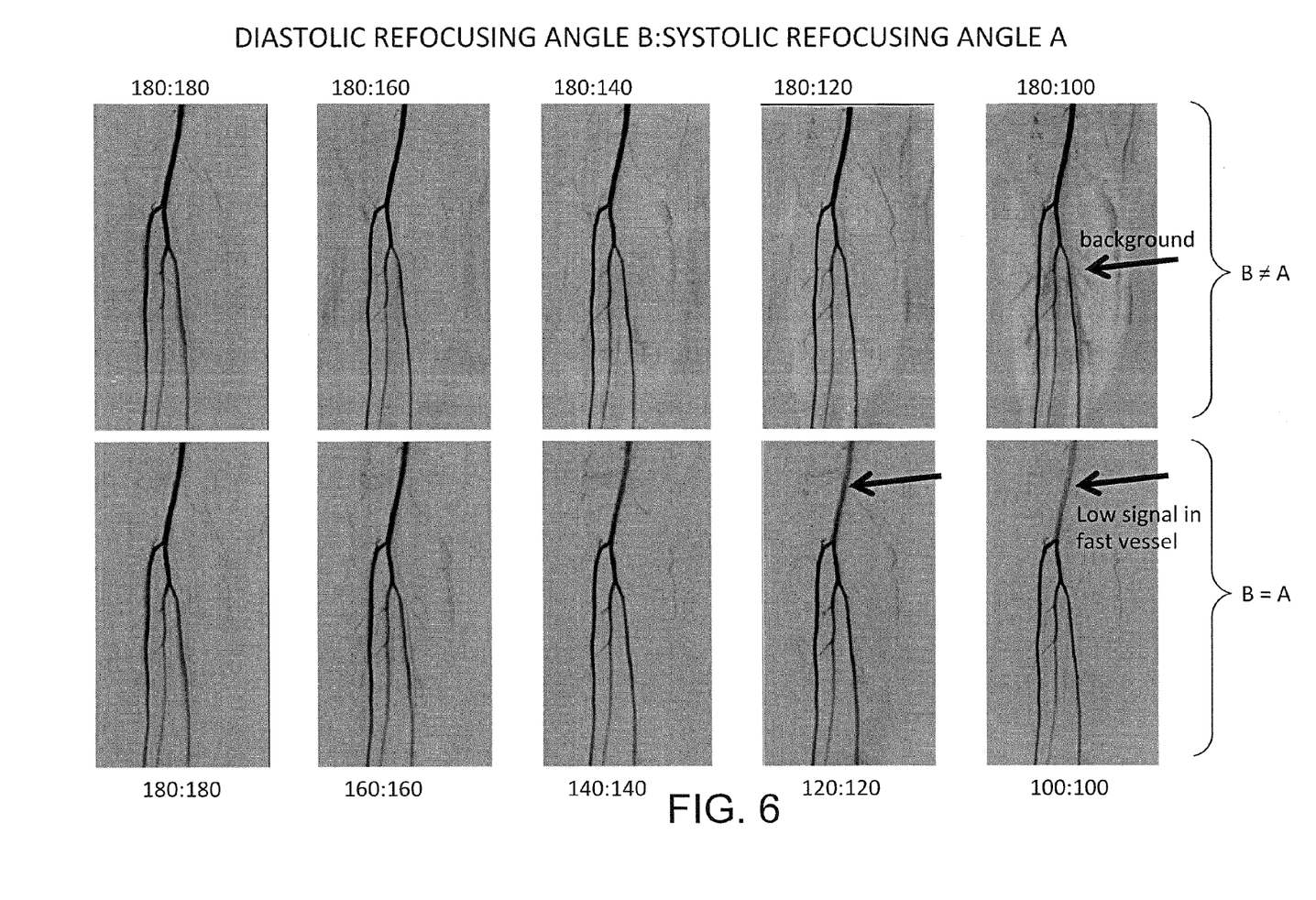

FIG. 6 shows similar results where a 180° maximum refocusing angle and data taken over a 4 RR interval (where RR=650 ms and 4 RR was needed to achieve 180').

Different refocusing angles maintained signal across the flow within the vessel—both fast and slow components. Something like 180°:120° or 160°:120° maintained good signal without too much background. Using 100° as the lower refocusing angle may introduce too much venous and background signal. In general, these FBI results showed small vessels quite well, even in classic FBI and provided consistent performance.

In flow-spoiled FBI, both systolic and diastolic scans typically have been acquired using the same sub-sequence parameter values for flow-spoiling, refocusing angle, etc. This has caused their subtraction to be somewhat suboptimal in terms of signal intensities of the arterial blood flows.

To improve this situation, improved operator controls are proposed. Two different sequences using a systolic sub-sequence with flow-spoiling and a diastolic sub-sequence with flow-compensation are independently selective in the user interface. Users are allowed to select a difference in, for example, refocusing angles to control arterial and venous signals, dephasing in not only the RO direction, but perhaps (if desired) in the PE direction as well. The two MRI sequences in a given FBI data acquisition (i.e., for each of the systolic and diastolic acquisition window sub-sequences) should, of course, be of the same type. However, the type of MRI sequence can also be chosen by operator input to be of any desired type of MRI data acquisition sequences like balanced steady-state free-precession (bSSFP), echo-planar imaging (EPI), etc.

This exemplary improved operator interface provides independent selectivity of two different MRA parameters for each of the sub-sequences (i.e., systolic and diastolic acquisitions in FS-FBI). The user selective GUI is preferably freely selective in the two sub-sequences. In this exemplary GUI, any desired flow-spoiling and/or refocusing angle parameters to be used in systolic and diastolic sub-sequences can be independently selected. This allows improvement of signal intensities of both arterial and venous in FBI-related acquisitions.

While the prior art operator interfaces have not allowed operators to freely and independently select these two MRA sequence parameters for systole and diastole in FBI, the exemplary embodiment does. This improves the final FBI signal intensities of arterial images after subtraction. The exemplary GUI permits at least two different sequence parameters to be independently set for systolic and diastolic sequences in FS-FBI. For example, the two parameters can be flow-compensation in the diastolic scan and flow-spoiling in the systolic scan. Different amounts of flow-spoiling in systolic and diastolic sequences can be associated with different RO gradient values and different refocusing angles in systolic and diastolic scans (e.g., such as a relatively low refocusing angle (e.g., 120°-140°) for the systolic scan and a relatively higher refocusing angle (e.g., 160°-180°) for the diastolic scan parameters).

For example, the two sequence parameters for systolic and diastolic scans can be optimized in an area of interest, such as the iliac region where, for example, it might be decided to make RO=−10% and 0% (diastolic, systolic), the thigh where RO=0%, +10% (diastolic, systolic), and the calf where RO=0%, +20% (diastolic, systolic). In addition, the refocusing angle variation concurrently can be for the iliac refocusing angles of 180°, 150° (diastolic, systolic) for the thigh refocusing angles of 180°, 140° (diastolic, systolic), and for the calf region of 180°, 130° (diastolic, systolic).

Freely selectable parameters are provided in an exemplary FBI GUI. Flow-spoiling control can be achieved in the systolic and diastolic acquisitions by independently controlling the amount of gradient flow-spoiling in each of the systolic and diastolic acquisitions and by independently controlling the refocusing angles for each of the systolic and diastolic acquisitions.

FIG. 7A illustrates an MRI system controller display screen on which an exemplary operator control graphical user interface (GUI) is presented. At 700, the operator is given a default choice for an MRI sequence type as an FSE type. However, the operator can chose another type of MRI sequence if desired for the systolic and diastolic data acquisition sequences to be utilized in a FS-FBI process.

Next, the GUI displayed in FIG. 7A presents the operator with completely independent separate choices of the RO gradient flow-spoiler pulse magnitude and the refocusing angle magnitude for each of the systolic acquisition sub-sequence and diastolic acquisition sub-sequence.

Figure 7B:
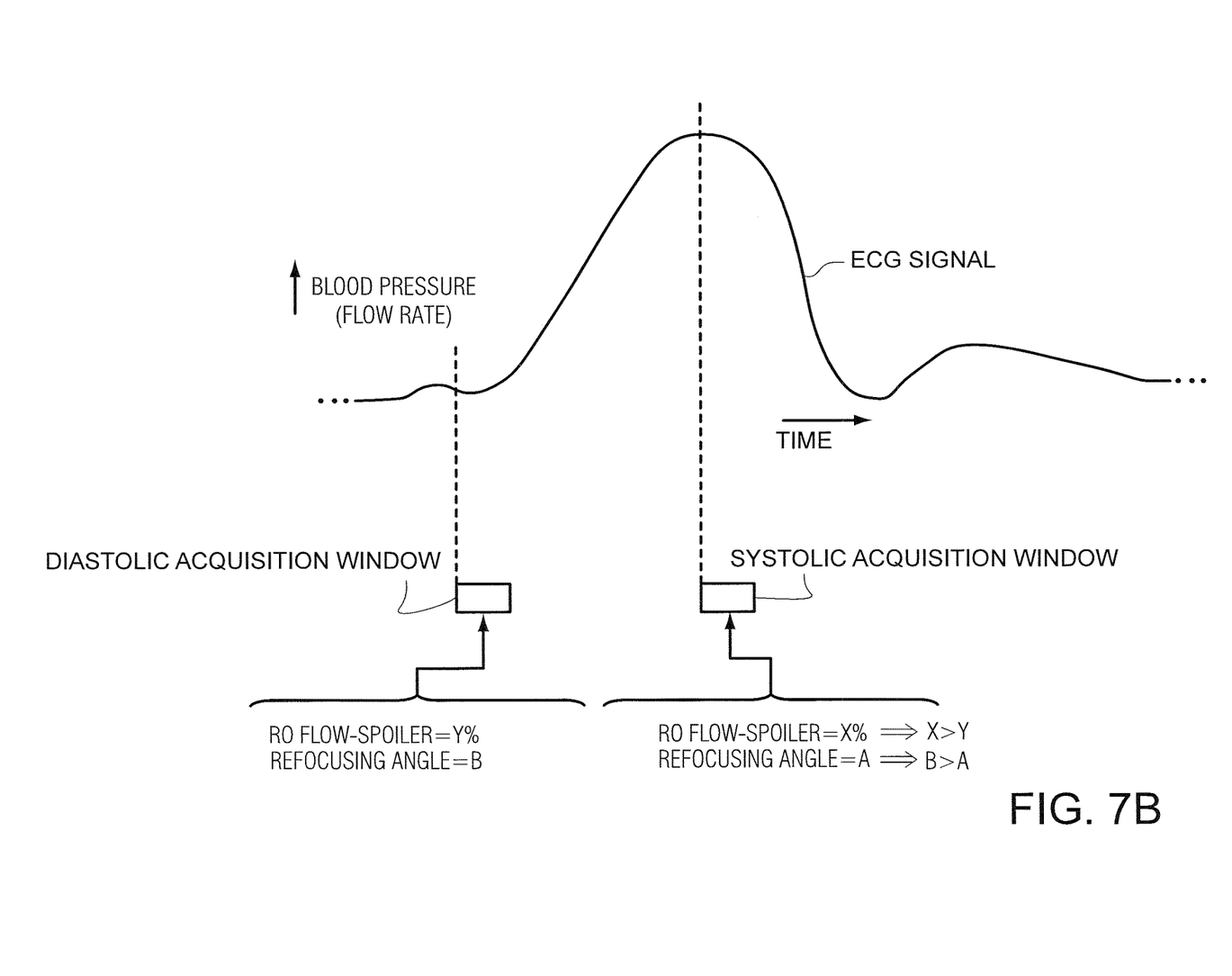
FIG. 7B schematically depicts systolic and diastolic data acquisition windows with respect to a schematic electrocardiogram (ECG) signal.

As depicted in FIG. 7B, the diastolic acquisition window occurs during a period of relatively low blood pressure and blood flow during the cardiac cycle while the systolic acquisition window is triggered to occur during a relatively high pressure and high flow period during the cardiac cycle. In FIG. 7A the operator is given an option at 702, 704, 706 and 708 to insert any desired parameter values for the RO gradient flow-spoiler magnitude and the refocusing angle for each of the systolic and diastolic MRI sub-sequences.

If desired, the GUI display screen may also include operator choices at 710, 712, 714 (etc.) for a region of interest (ROI) having preset default values for the gradient flow-spoiler magnitudes and refocusing angles. As depicted in FIG. 7A, the default values for the iliac may have systolic and diastolic parameter values displayed. Different default values would be available for the operator if the femoral (thigh) ROI is chosen. Similarly, a different set of parameter values would be defaulted for the calf region. Of course, even if the default values are initially selected by choosing a particular ROI, the operator still has the ability to independently change any of the default values as desired at 716. At 718, the operator is given an option for adding some phase-encode (PE) magnetic gradient flow-spoiler pulse independently for the systolic and/or diastolic sub-sequence acquisitions. At 720, the operator is given an option to store the current parameter values for future use (using a default or specified file name).

Figure 8:
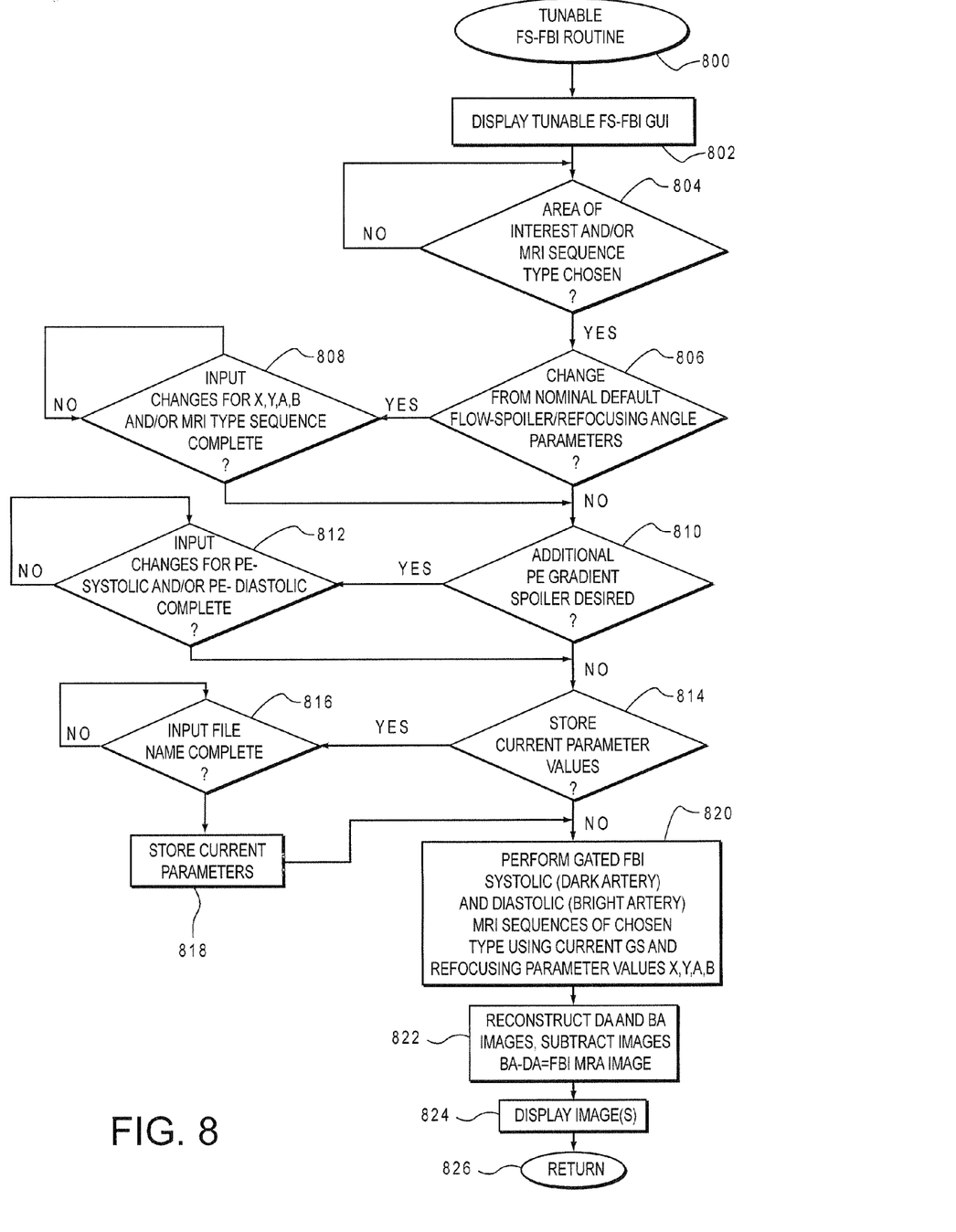
FIG. 8 schematically depicts an exemplary executable computer program control code structure for use in the MRI system of FIG. 1 to effect the exemplary GUI of FIG. 7A.

FIG. 8 provides a schematic flow chart depiction of suitable computer program logic code structure for achieving the exemplary GUI display screen depicted at FIG. 7A. The tunable FS-FBI routine is entered at 800 (i.e., from an overarching operating system or the like as will be appreciated by those in the art) and the control display tunable FS-FBI GUI is displayed at 802. At 804, a wait loop is entered until the area of interest and/or MRI sequence type has been chosen. Next, a test is made at 806 to see if the operator desires to change from the nominal default values for the gradient flow-spoiling and/or refocusing angle parameters. If so, then a wait loop is entered at 808 while the operator inputs desired changes to the parameter values and/or MRI sequence type. Once this has been completed, then a test is made at 810 to determine if an additional PE flow-spoiler gradient is desired. If so, then a wait loop is entered at 812 while the operator inputs changes for the PE in systolic and/or diastolic acquisition windows. Once that is completed, control is returned to the main path of the flow chart at 814 (which is, of course, also entered if no additional PE flow-spoiler is desired), where a test is made to see if the operator desires to store current parameter values. If so, then a wait loop is entered at 816 for the operator to input any desired file name in lieu of the default name. Once that has been completed, then the current parameters are stored at 818 and control is again returned to the main control flow path at 820 (which is, of course, also entered if the operator does not desire to store current parameter values for future use).

At 820, the thus tuned FS-FBI data acquisition sequences (i.e., involving MRI sub-sequences for data acquisition windows in the systolic and diastolic windows) of the chosen type using the currently designated gradient flow-spoiling and refocusing angle parameter values is performed (in accordance with conventional practices, but using the tuned parameter choices entered by the operator via the GUI of FIG. 7A).

Thereafter, at 822, the usual reconstruction of DA and BA images and subtraction is performed and the resulting FBI image is displayed at 824 before control is returned at 826 to the calling system.

Of course, as will be appreciated by those in the art, the MRI system controller could be configured by suitable similar programming to use different gradient flow-spoiling and refocusing angle parameter values for the systolic and diastolic FS-FBI acquisition sub-sequences—with or without use of a flexible controller input GUI such as depicted in FIG. 7A. For example, different systolic and diastolic gradient flow-spoiling and refocusing angle parameter values for different FS-FBI circumstances (e.g., type of patient, ROI, age of patient, condition of patient, etc) could be pre-determined and then automatically invoked by the MRI system controller upon command and/or perhaps even upon automatic detection of then existing circumstances.

In the past, the RO flow-spoiler gradient has been changed as a function of flow speed but the same flow-spoiler gradient magnitude was used for both systolic and diastolic acquisition windows. Now, with the improved GUI, the operator may use different RO flow-spoiler gradient magnitudes in the diastolic and systolic acquisition windows. For example, in the diastolic acquisition window, the RO flow-spoiler might have no effective change, while for the systolic acquisition window, the RO flow-spoiler may have a +20% value.

While prior art approaches did also permit one to use different refocusing angles and RO flow-spoiler magnitudes for different patients, such independent control of refocusing angle and RO flow-spoiler magnitude within the same FS-FBI acquisition scan (which inherently contains both systolic and diastolic sub-acquisition windows), required use of the same RO flow-spoiler and refocusing angle parameter values for both systolic and diastolic acquisitions. Now, however, the operator might choose a refocusing angle of 120° for systolic sub-acquisitions and 160° for diastolic sub-acquisitions. In short, the present improved operator-controlled GUI permits different RO flow-spoiler and refocusing angle values to be used in the systolic and diastolic sub-acquisition windows within a single FS-FBI data acquisition sequence.

In short, the operator is free to tune sub-acquisition parameters to be different within a single FS-FBI sequence so as to maximize signal difference between the systolic and diastolic images.

In one embodiment, an RO gradient providing partial flow-compensation (e.g., RO spoiler=−10%) or a non-spoiler (e.g., RO spoiler=0%) may be used for the diastolic window with flow-spoiling (e.g., RO spoiler=+10%) in other situations. For example, in a faster flow area like the iliac, one may use an RO spoiler=+10% during the diastolic window and an RO spoiler=0% during the systolic window. For the thigh region, the RO spoiler may be 0% in the diastolic window and +10% in the systolic window. For the calf region, the RO spoiler may be +10% during the diastolic window, but be +20% during the systolic window.

Although FSE MRI sequences are typically used for FS-FBI, other MRI data acquisition sequences may be used for the systolic and diastolic sub-sequences within an overall FS-FBI acquisition sequence. Of course, the same MRI sequence type should be used for both the systolic and diastolic sub-sequences within a given single overall FS-FBI acquisition sequence. Other possible MRI sequence types would be, for example, bSSFP, EPI, etc. In any event, the controlling parameters for these different types of MRI sequences may be different and yet similar to the RF excitation, RF refocusing, RO flow-spoiler gradient, etc. parameters of the FSE MRI data acquisition sequence. As those in the art will appreciate, in that event, the exemplary GUI of FIG. 7A would be modified so as to include suitable independent parameter choices for systolic and diastolic sub-sequences appropriate to each chosen type of MRI data acquisition sequence to be used.

The exemplary embodiments can be modified to use the Variable Flip Angle (VFA) technique and/or to use different sweep patterns of VFA for each of systolic and diastolic phase images. For example, if diastolic triggering is used, a constant refocusing flip angle may be preferred, while for systolic triggering, the VFA technique may be preferred. The constant flip angle can be expected to give good bright blood diastolic images, while VFA can be expected to accelerate the flow-spoiling effect in systolic images.

As those in the art will appreciate, while gradient flow spoiler (FS) pulses are part of exemplary FBI embodiments, such are not essential to all possible FBI implementations of the present invention.

While certain embodiments of the invention have been described, these embodiments have been presented by way of example only, and are not intended to limit the scope of the invention. Indeed, the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A magnetic resonance imaging (MRI) system comprising:
   an MRI gantry assembly having static magnet, gradient magnet, RF coil and patient support structures configured to define an imaging volume about a region of interest in a patient;
   an MRI control system connected to said MRI gantry and configured to control components thereof to effect plural magnetic resonance angiography (MRA) data acquisition sequences including cardiac triggered images associated with systolic and diastolic phases of the cardiac cycle; and
   image reconstruction processing and display components including at least one processor configured to reconstruct and process images of patient anatomy within said region of interest using MRI data acquired by said plural MRA data acquisition sequences and to display a plurality of resultant MRA difference images resulting therefrom;
   said MRI control system including at least one programmed computer processor configured to independently control at least one imaging sequence parameter so as to (1) use different flip angles of RF refocusing pulses while acquiring data for each of respectively associated systolic and diastolic phase images in each of a plurality of overall MRA data acquisition sequences, each sequence comprising a repeating plurality of first and second interleaved subsequence pairs, each subsequence including an RF excitation pulse followed by a plurality of RF refocusing pulses, wherein a first flip angle is used for the first subsequences while acquiring systolic phase images and a different second flip angle is used for the second subsequences while acquiring diastolic phase images, said first and second flip angles being unequal and thus different from each other, and (2) for at least the subsequence that acquires data for the systolic phase in successive ones of said overall MRA data acquisition sequences, configure respectively associated re-focusing flip angles according to a variable flip angle (VFA) sweep pattern.

2. A magnetic resonance imaging (MRI) system as in claim 1, wherein said MRI control system is configured to have at least one operator input and display interface which are configured to provide operator options for independently controlling at least one imaging sequence parameter for each of systolic and diastolic phase images in the plurality of overall MRI data acquisition sequences.

3. An MRI system as in claim 1, wherein:
   said at least one of said MRA data acquisition sequences comprises a fast spin echo (FSE) MRI data acquisition sequence having an initial nuclear magnetic resonance (NMR) RF (radio frequency) excitation pulse followed by a succession of refocusing RF refocusing pulses with interspersed NMR RF spin echoes respectively associated with magnetic gradient pulses including spoiler pulse components; and
   said at least one imaging sequence parameter comprises (a) an added read-out (RO) magnetic gradient flow-spoiler pulse component effective magnitude and (b) refocusing pulse effective magnitude.

4. An MRI system as in claim 2, wherein:
   said operator input and display interface is configured to also provide default values for said at least one imaging sequence parameter and an operator option to change said default values.

5. An MRI system as in claim 4, wherein:
   said operator input and display interface is configured to also provide operator options for a plurality of different regions of interest in the patient, each of said regions of interest having its own respective said default values for said at least one imaging sequence parameter and an operator option to change said default values.

6. An MRI system as in claim 5, wherein:
   at least one of said MRA data acquisition sequences comprises a fast spin echo (FSE) MRI data acquisition sequence having an initial nuclear magnetic resonance (NMR) RF (radio frequency) excitation pulse followed by a succession of RF refocusing pulses with interspersed NMR RF spin echoes respectively associated with magnetic gradient pulses including flow-spoiler pulse components;
   said at least one imaging sequence parameter comprises (a) an added read-out (RO) magnetic gradient flow-spoiler pulse component effective magnitude and (b) refocusing pulse effective magnitude; and
   said different regions of interest and associated default values for the gradient flow-spoiler pulses and refocusing pulses comprise:

| ROI | RO gradient flow-spoiler | refocusing angle |
|---|---|---|
| iliac | systolic = A %<br>diastolic = B % | systolic = G°<br>diastolic = H° |
| femoral | systolic = C %<br>diastolic = D % | systolic = I°<br>diastolic = J° |
| calf | systolic = E %<br>diastolic = F % | systolic = K°<br>diastolic = L° | where at least two of A, C and E have different values,
at least two of G, I and K have different values,
the stated A, B, C, D, E and F gradient flow-spoiler percentages each represent a change in RO magnetic gradient pulse effective magnitude in the FSE MRI sequence by the stated percentage, and
the stated G, H, I, J, K and L refocusing angles in degrees each represent an effective magnitude for the RF refocusing pulses sufficient to provide the stated angle as measured in degrees of NMR nuclei spin nutation.

7. An MRI system as in claim 6, where A=+10%; B=0%; C=+20%; D=0%; E=+25%; F=0%; G=140°; H=170°; I=130°; J=170°; K=120° and L=170°.

8. An MRI system as in claim 2, wherein said operator input and display interface is configured to provide an operator option to designate one of plural types of MRI data acquisition sequences to be used in acquiring both the images associated with the systolic and diastolic phases of cardiac cycles.

9. An MRI system as in claim 2, wherein said operator input and display interface is configured to provide an operator option to include an additional component of magnetic gradient flow-spoiler pulse along a phase encode (PE) direction, said component being independently controllable for the systolic and diastolic phase images.

10. An MRI system as in claim 2, wherein said operator input and display interface is configured to provide an operator option to store for future use the data acquisition parameters selected for current use.

11. A magnetic resonance imaging (MRI) method comprising:
configuring an MRI gantry assembly having static magnet, gradient magnet, RF coil and patient support structures to define an imaging volume about a region of interest in a patient;
controlling components of said MRI gantry assembly to effect plural magnetic resonance angiography (MRA) data acquisition sequences including cardiac triggered images associated with systolic and diastolic phases of the cardiac cycle while independently controlling at least one imaging sequence parameter so as to (1) use different flip angles of RF refocusing pulses while acquiring data for each of respectively associated systolic and diastolic phase images in each of a plurality of overall FBI MRI data acquisition sequence each sequence comprising a repeating plurality of first and second subsequence pairs, each subsequence including an RF excitation pulse followed by a plurality of RF refocusing pulses, wherein a first flip angle is used for the first subsequences while acquiring systolic phase images and a different second flip angle is used for the second subsequences while acquiring diastolic phase images said first and second flip angles being unequal and thus different from each other, and (2) for at least the subsequence that acquires data for the systolic phase in successive ones of said overall MRA data acquisition sequences, configure respectively associated re-focusing flip angles according to a variable flip angle (VFA) sweep pattern; and
reconstructing and processing an image of patient anatomy within said region of interest using MRI data acquired by said MRA data acquisition sequences and to display an image resulting therefrom.

12. An MRI method as in claim 11, further comprising:
configuring at least one operator input and display interface to provide operator options for independently controlling at least one imaging sequence parameter for each of systolic and diastolic phase images in an MRI data acquisition sequence.

13. An MRI method as in claim 11, wherein:
said at least one of said MRA data acquisition sequences comprises a fast spin echo (FSE) MRI data acquisition sequence having an initial nuclear magnetic resonance (NMR) RF (radio frequency) excitation pulse followed by a succession of RF refocusing pulses with interspersed NMR RF spin echoes respectively associated with magnetic gradient pulses including flow spoiler pulse components; and
said at least one imaging sequence parameter comprises (a) an added read-out (RO) magnetic gradient flow-spoiler pulse component effective magnitude and (b) refocusing pulse effective magnitude.

14. An MRI method as in claim 12, further comprising:
configuring said operator input and display interface to also provide default values for said at least one imaging sequence parameter and an operator option to change said default values.

15. An MRI method as in claim 14, further comprising:
configuring said operator input and display interface to also provide operator options for a plurality of different regions of interest in the patient, each of said regions of interest having its own respective said default values for said at least one imaging sequence parameter and an operator option to change said default values.

16. An MRI method as in claim 15, wherein:
at least one of said MRA data acquisition sequences comprises a fast spin echo (FSE) MRI data acquisition sequence having an initial nuclear magnetic resonance (NMR) RF (radio frequency) excitation pulse followed by a succession of RF refocusing pulses with interspersed NMR RF spin echoes respectively associated with magnetic gradient pulses including flow-spoiler pulse components;
said at least one imaging sequence parameter comprises (a) an added read-out (RO) magnetic gradient flow-spoiler pulse component effective magnitude and (b) refocusing pulse effective magnitude; and
said different regions of interest and associated default values for the gradient flow-spoiler pulses and refocusing pulses comprise:

| ROI | RO gradient flow spoiler | refocusing angle |
|---|---|---|
| iliac | systolic = A %<br>diastolic = B % | systolic = G°<br>diastolic = H° |
| femoral | systolic = C %<br>diastolic = D % | systolic = I°<br>diastolic = J° |
| calf | systolic = E %<br>diastolic = F % | systolic = K°<br>diastolic = L° | where
at least two of A, C and E have different values,
at least two of G, I and K have different values, the stated A, B, C, D, E and F gradient flow-spoiler percentage represents a change in RO magnetic gradient pulse effective magnitude in the FSE MRI sequence by the stated percentage, and the stated G, H, I, J, K and L refocusing angle in degrees represents an effective magnitude for the refocusing RF pulses sufficient to provide the stated nutation angle as measured in degrees of NMR nuclei spin nutation.

17. An MRI method as in claim 16, where A=+10%; B=0%; C=+20%; D=0%; E=+25%; F=0%; G=140°; H=170°; I=130°; J=170°; K=120° and L=170°.

18. An MRI method as in claim 12, further comprising configuring said operator input and display interface to provide an operator option to designate one of plural types of MRI data acquisition sequences to be used in acquiring both the images associated with the systolic and diastolic phases of the cardiac cycle.

19. An MRI method as in claim 12, further comprising configuring said operator input and display interface to provide an operator option to include an additional component of magnetic gradient flow spoiler pulse along a phase encode (PE) direction, said component being independently controllable for the systolic and diastolic phase images.

20. An MRI method as in claim 12, further comprising configuring said operator input and display interface to provide an operator option to store for future use the data acquisition parameters selected for current use.

21. The MR1 system according to claim 1, wherein said at least one programmed computer processor is further configured to independently control both said first subsequence and said second subsequence in successive ones of said overall MRA data acquisition sequences, to use respectively associated re-focusing flip angles according to a VFA sweep pattern.

22. The MRI method according to claim 11 wherein said at least one programmed computer processor is further configured to independently control both said first subsequence and said second subsequence in successive ones of said overall MRA data acquisition sequences, to use respectively associated re-focusing flip angles according to a VFA sweep pattern.

* * * * *